United States Patent [19]

Cordier

[11] Patent Number: 5,023,384
[45] Date of Patent: Jun. 11, 1991

[54] PROCESS FOR THE PREPARATION OF TRIFLUOROETHANOL

[75] Inventor: Georges Cordier, Francheville, France

[73] Assignee: Rhone-Poulenc Chimie, Courbevoie Cedex, France

[21] Appl. No.: 424,713

[22] Filed: Oct. 20, 1989

[30] Foreign Application Priority Data

Oct. 21, 1988 [FR] France ................................ 88 13797

[51] Int. Cl.$^5$ ...................... C07C 29/136; C07C 31/38
[52] U.S. Cl. .................................................. 568/842
[58] Field of Search ......................................... 568/842

[56] References Cited

U.S. PATENT DOCUMENTS 4,533,771 8/1985 Cordier .............................. 568/842

Primary Examiner—Howard T. Mars
Attorney, Agent, or Firm—Finnegan, Henderson, Farabow, Garrett, and Dunner

[57] ABSTRACT

The present invention relates to a process for the industrial preparation of trifluoroethanol by passage of a reaction mixture containing trifluoroacetic acid, water and trifluoroethanol over a percolating fixed bed consisting of a rhodium- or ruthenium-based catalyst.

14 Claims, No Drawings

PROCESS FOR THE PREPARATION OF TRIFLUOROETHANOL

GENERAL BACKGROUND

The present invention relates to a process for the preparation of trifluoroethanol. It relates more particularly to a process for the preparation of trifluoroethanol by the hydrogenation of trifluoroacetic acid.

It is known to prepare perfluoroalkylated alcohols from the corresponding acids by at least two techniques; the first involves acids in the vapor phase, the second involves acids in the liquid phase.

According to the first technique described, for example, in U.S. Pat. Nos. 3,390,191 and 4,273,947, the perfluoroalkylated carboxylic acid in the gaseous form is put into contact with a chrome- or copper-based catalyst (U.S. Pat. No. 3,390,191) or a rhodium- or iridium-based catalyst (U.S. Pat. No. 4,273,947) at a temperature of between the boiling point of the acid and 400° C. The two patents describe only the hydrogenation of trifluoroacetic acid, and the yields given are often low; 1.4% according to U.S. Pat. No. 4,273,947 and 37% according to U.S. Pat. No. 3,390,191. A continuous process for hydrogenation of trifluoroacetic acid, such as described in U.S. Pat. No. 4,396,784, is also known, which consists in hydrogenating this acid on a rhenium—based catalyst deposited in a weight ratio of 3.3% on a fluorinated alumina. The process is carried out at a temperature of 280° C. at a pressure of 20 bars.

The chemical industry prefers to use processes in the liquid phase because of the low yields, the temperatures required to obtain these yields and the technology required for the implementation of reactions in the gaseous phase.

The second technique for the preparation of trifluoroethanol in the liquid phase had been described, in particular, in U.S. Pat. Nos. 3,663,629 and 4,273,947. According to these patents perfluoroalkylcarboxylic acid and hydrogen are put in contact in an autoclave with a catalyst chosen from ruthenium (U.S. Pat. No. 3,663,629) and rhodium or iridium (U.S. Pat. No. 4,273,947). The hydrogen pressure used is very high in U.S. Pat. No. 3,663,629, preferably between 40 and 400 bars. In U.S. Pat. No. 4,273,947 the hydrogen pressure is much lower, preferably between 5 and 15 bars. In either patent, the quantity by volume of acid introduced, calculated with respect to the total volume of the reactor, which is 1%, would not allow industrial production. All of the processes for hydrogenation by a liquid phase technique are difficult to extrapolate to the industrial scale since they are always discontinuous processes which necessitate emptying and cleaning times for the reactors, thereby increasing the price of the final product.

All these documents prove that the solution to the problem which the industry seeks to resolve, that is, to have a continuous process for the preparation of trifluoroethanol from trifluoroacetic acid in the liquid phase using a catalyst which is readily available and with excellent yields, is not obvious.

SUMMARY OF THE PRESENT INVENTION

The present invention, has the above-stated objective to be attained. The present invention provides a process for the preparation of trifluoroethanol by the hydrogenation of trifluoroacetic acid in the presence of a rhodium- or ruthenium-based catalyst, wherein the trifluoroacetic acid, in solution in a water/trifluoroethanol mixture, is continuously introduced by trickling said solution onto a fixed bed comprising a catalytic metal deposited on a support at a concentration of between about 0.5 and 5% with respect to the support in the presence of hydrogen, and at a temperature of between about 60° and 150° C., at a pressure less than 50 bars. The concentration of the catalytic metal is preferably between about 0.5 and 2%. The pressure is preferably between about 15 and 50 bars.

The solution which is continuously introduced onto the fixed bed preferably has the following composition in moles:

| | |
|---|---|
| trifluoroacetic acid | 5 to 50 parts |
| trifluoroethanol | 25 to 47.5 parts |
| water | 25 to 47.5 parts |

It is most preferred to use a solution containing trifluoroacetic acid diluted in an equimolar water/trifluoroethanol mixture.

The rhodium- or ruthenium-based catalyst is deposited on a support consisting of silica, charcoal or alumina.

It is preferable to use a rhodium-based catalyst deposited on charcoal.

The quantity of catalytic metal deposited on the support is preferably between 0.1 and 2% by weight.

The particle size of the support is preferably between 1 and 5 mm, and more preferably between 2 and 4 mm. This support can be in various forms: spheres, short rods, fragments or flakes.

The hydrogen is introduced pure or in a mixture with a gas as nitrogen or methane which is inert under the reaction conditions. The reactor consists of one or more cylindrical tubes having a diameter of between 3 and 40 cm. The height of the industrial tube advantageously varies between 2 and 10 meters and preferably between 4 and 7 meters. In one embodiment, the catalyst bed is composed of one or more cylindrical tubes having a diameter of between 3 and 4 cm and a length of between about 20 and 10 meters. The reactor is preferably provided with a jacket containing a heat-carrying fluid. It is fed with the liquid fluid consisting of the reaction mixture at a flow rate such that, as a function of the diameter of the tube, the linear speed of the liquid phase, considered with respect to the diameter of the empty tube, is between about 0.2 and 10 mm s$^{-1}$, and preferably between about 1 and 5 mm s$^{-1}$.

The flow rate of hydrogen or of the vector gas containing the hydrogen is determined by the formula:

$$Q_r = (Q_2 \times P_{bar}) \times 1.4$$

in which $Q_2$ is the flow rate of the liquid in liters/hour and P is the pressure applied in the tube in bars.

$Q_r$, expressed in liter/hours, signifies the flow rate of gas at NTP (normal temperature and pressure).

According to a preferable process of implementation, the liquid and the gas are introduced into the tubes in co-current. They can also, without going outside the scope of the present invention, be introduced in countercurrent. To avoid temperature heterogeneities in the whole of the catalytic bed, it is preferable to heat the reagents to a temperature about 10° C. lower than the temperature of hydrogenation prior to introduction into the tubes.

The liquid and the gas which flow out of the column are then cooled and separated. It is preferable to separate the phases by the difference in boiling point between the two phases. In the case in which conversion is incomplete and some trifluoroacetic acid still remains, a second passage over the catalytic bed is advised.

Hydrogenation under the conditions of the present invention produces almost no by-products (less than 0.5%).

The invention will be more completely described with the aid of the following examples which should not be considered as limiting the invention.

EXAMPLE 1

The reactor consisted of a tube of Hastelloy "C" material which resists hot trifluoroacetic acid. It was designed to resist. pressures greater than or equal to 150 b. Its interior diameter is 2.6 cm and its height is 100 cm.

It was filled with 0.5 liter of catalyst, which is, according to the density of the catalyst, approximately 185 to 195 g. The preferred catalyst is a catalyst containing 1% w/w of rhodium deposited on a charcoal of high specific surface area (1,000 $m^2g^{-1}$) and presented in grains of 3 to 4 mm diameter and 3 to 5 mm length.

The trifluoroacetic acid and the hydrogen are fed from the top to the bottom in co-current in a controlled quantity.

The following succession of operations is carried out in the reactor described above and filled with the 1% Rh/C catalyst (196 g):

Nitrogen purge at 20 l/h (1 h) followed by hydrogen purge at 20 l/h at ambient temperature.

Injection of distilled water at 90° C./hydrogen at 20 b: 8 hours at a rate of 1 $l/h^{-1}$.

THEN:

Injection of a mixture having the following composition (mole/mole):

| | |
|---|---|
| Trifluoroacetic acid | 25% |
| Water | 37.5% |
| Trifluorethanol | 37.5% |

This composition is not critical, and trifluoroacetic acid can be injected in the pure state or, may be largely diluted in water.

The temperature of the bed is taken to 120° C. and the total pressure to 40 bars.

The flow rate of the liquid mixture is taken to 2 l/h. The flow rate of the hydrogen is taken to 110 l $h^{-1}$ NTP. The effluent liquid mixture recovered at the bottom of the bed is analyzed by acidimetry and gas phase chromatography, then recycled. The effluent gaseous mixture is also analyzed.

Products such as $CF_3CH_3$, $C_2H_6$, $CH_4$ resulting from the hydrogenolysis of the oxygen-containing molecules are measured by gas phase chromatography.

RESULTS

| NUMBER OF PASSAGES OVER THE CATALYTIC BED | TFE/ TFA + TFE mole/mole | DC % TFA | ACTIVITY MOLES TFE FORMED $h^{-1}KG^{-1}$ catalyst |
|---|---|---|---|
| 1 | 0.78 | 45 | 21.5 |
| 2 | 0.9 | 75 | 14.9 |
| 3 | 0.96 | 90 | 7.5 |
| 4 | 0.993 | 98.3 | 3.0 |

The yield of the secondary conversion as the sum ($CH_4+C_2H_6+CF_3CH_3$) is constantly between 0.3 and 0.5% of the trifluoroacetic acid used, which confers on this reaction a selectivity $\geq 99.5\%$ for the formation of trifluoroethanol.

EXAMPLE NO. 2

Example 1 is repeated at 90° C. and at 40 bars of total pressure. At the end of 8 passages over the catalytic bed the conversion rate of the trifluoroacetic acid is 98.9%, and the yield of trifluoroethanol is 99.9% with respect to the trifluoroacetic acid converted.

EXAMPLE NO. 3

Example No. 1 is repeated at 120° C. and at 20 bars total pressure.

At the end of 8 passages over the catalytic bed the conversion rate of the trifluoroacetic acid is 99.3% and the yield of trifluoroethanol with respect to the trifluoroacetic acid used is 99.6%.

I claim:

1. A continuous process for the preparation of trifluoroethanol comprising hydrogenating trifluoroacetic acid in solution in a water/trifluoroethanol mixture by passing said mixture more than once over a rhodium- or ruthenium-based catalyst in the presence of hydrogen.

2. The process of claim 1, wherein the trifluoroacetic acid solution is continuously introduced by trickling said solution onto the catalyst deposited on a support and in a fixed bed.

3. The process of claim 2 wherein the catalyst is deposited on the support at a concentration of between 0.5 and 5%, with respect to the support, in the presence of hydrogen and at a temperature of between about 60° and 150° C., at a pressure less than about 50 bars.

4. The process of claim 3 wherein the catalyst is deposited on the support in a concentration of between 0.5 and 2%, with respect to the support.

5. The process of claim 3 wherein the pressure is between about 15 and 50 bars.

6. The process of claim 1, wherein the trifluoroacetic acid is introduced in a mixture having the following composition in moles:

| | |
|---|---|
| trifluoroacetic acid | 5 to 50 parts |
| trifluoroethanol | 25 to 47.5 parts |
| water | 25 to 47.5 parts. |

7. The process of claim 1, wherein the trifluoroacetic acid is introduced in an equimolar water/trifluoroethanol mixture.

8. The process of claim 3, wherein the support is silica, charcoal or alumina.

9. The process of claim 8, wherein the support is charcoal.

10. The process of claim 8, wherein the support has a particle, size of between about 1 and 5 mm.

11. The process of claim 10, wherein the support has a particle size of between 2 and 4 mm.

12. The process of claim 2, wherein the catalyst bed is composed of one or more cylindrical tubes having a diameter of between about 3 and 40 cm and a length of between about 2 and 10 meters.

13. The process of claim 1, wherein the speed of passage of the liquid phase in the catalytic tube is between 0.2 and 10 mm $s^{-1}$.

14. The process of claim 13, wherein the speed of passage is between 1 and 5 mm $s^{-1}$.

* * * * *

UNITED STATES PATENT AND TRADEMARK OFFICE
CERTIFICATE OF CORRECTION

PATENT NO. : 5,023,384

DATED : June 11, 1991

INVENTOR(S) : Georges Cordier

It is certified that error appears in the above-identified patent and that said Letters Patent is hereby corrected as shown below:

Claim 10, column 4, line 57, delete "," after --particle--.

Signed and Sealed this

Sixth Day of April, 1993

Attest:

STEPHEN G. KUNIN

*Attesting Officer*     *Acting Commissioner of Patents and Trademarks*